(12) United States Patent
Malchow et al.

(10) Patent No.: US 9,375,204 B2
(45) Date of Patent: *Jun. 28, 2016

(54) BIOPSY SYSTEM WITH INTEGRATED IMAGING

(71) Applicant: SenoRx, Inc., Tempe, AZ (US)

(72) Inventors: Lloyd H. Malchow, San Juan Capistrano, CA (US); Paul Lubock, Monarch Beach, CA (US); Derek Daw, Huntington Beach, CA (US)

(73) Assignee: SENORX, INC., Tempe, AZ (US)

( * ) Notice: Subject to any disclaimer, the term of this patent is extended or adjusted under 35 U.S.C. 154(b) by 125 days.

This patent is subject to a terminal disclaimer.

(21) Appl. No.: 14/148,605

(22) Filed: Jan. 6, 2014

(65) Prior Publication Data

US 2014/0121504 A1 May 1, 2014

Related U.S. Application Data

(63) Continuation of application No. 11/810,425, filed on Jun. 5, 2007, now Pat. No. 8,622,907.

(60) Provisional application No. 60/810,906, filed on Jun. 5, 2006.

(51) Int. Cl.
*A61B 8/00* (2006.01)
*A61B 10/02* (2006.01)
(Continued)

(52) U.S. Cl.
CPC ............ *A61B 10/0283* (2013.01); *A61B 8/0833* (2013.01); *A61B 8/0841* (2013.01); *A61B 8/4405* (2013.01); *A61B 8/4472* (2013.01); *A61B 2017/00199* (2013.01)

(58) Field of Classification Search
CPC ................. A61B 10/0283; A61B 2017/00199; A61B 2019/5276; A61B 8/0833; A61B 8/0841
See application file for complete search history.

(56) References Cited

U.S. PATENT DOCUMENTS 3,844,272 A 10/1974 Banko
4,517,976 A 5/1985 Murakoshi et al.
(Continued)

FOREIGN PATENT DOCUMENTS

DE 3703218 A1 8/1988
EP 0225973 A2 6/1987
(Continued)

OTHER PUBLICATIONS

Amplifiermodule 1-30MHz 150Watts, LCF Enterprises RF Power Amplifiers, www.lcfamps.com, pp. 1-2, 1998.
(Continued)

*Primary Examiner* — Baisakhi Roy (57) ABSTRACT

A structurally integrated biopsy system includes a movable base having wheels to facilitate movement of the structurally integrated biopsy system. On the movable based there is mounted a tissue removal system, an ultrasound imaging system, and a controller. The tissue removal system includes a probe connector configured to connect to a tissue removal probe. The ultrasound imaging system is configured to generate an ultrasound image of a body region of a patient, and has an image display system having an image display screen to display ultrasound images taken by the ultrasound imaging system. The controller is configured to be in communication with each of the tissue removal system and the ultrasound imaging system to both provide control information for the ultrasound imaging system and provide control information for the tissue removal system in the structurally integrated biopsy system.

20 Claims, 6 Drawing Sheets

(51) Int. Cl.
*A61B 8/08* (2006.01)
*A61B 17/00* (2006.01)

(56) References Cited

U.S. PATENT DOCUMENTS

| | | | |
|---|---|---|---|
| 4,658,819 A | 4/1987 | Harris et al. | |
| 4,739,759 A | 4/1988 | Rexroth et al. | |
| 4,878,493 A | 11/1989 | Pasternak et al. | |
| 5,159,929 A | 11/1992 | Morris et al. | |
| 5,335,671 A | 8/1994 | Clement | |
| 5,400,267 A | 3/1995 | Denen et al. | |
| 5,415,169 A | 5/1995 | Siczek et al. | |
| 5,615,682 A * | 4/1997 | Stratz, Sr. | 600/459 |
| 5,617,857 A | 4/1997 | Chader et al. | |
| 5,640,956 A | 6/1997 | Getzinger et al. | |
| 5,749,869 A | 5/1998 | Lindenmeier et al. | |
| 5,769,086 A | 6/1998 | Ritchart et al. | |
| 5,772,659 A | 6/1998 | Becker et al. | |
| 5,849,009 A | 12/1998 | Bernaz | |
| 5,976,128 A | 11/1999 | Schilling et al. | |
| 5,997,535 A | 12/1999 | Betsill et al. | |
| 6,022,347 A | 2/2000 | Lindenmeier et al. | |
| 6,036,681 A | 3/2000 | Hooven | |
| 6,063,035 A * | 5/2000 | Sakamoto et al. | 600/462 |
| 6,066,134 A | 5/2000 | Eggers et al. | |
| 6,117,126 A | 9/2000 | Appelbaum et al. | |
| 6,120,462 A | 9/2000 | Hibner et al. | |
| 6,162,216 A | 12/2000 | Guziak et al. | |
| 6,325,759 B1 | 12/2001 | Pelissier | |
| 6,370,411 B1 | 4/2002 | Osadchy et al. | |
| 6,391,024 B1 | 5/2002 | Sun et al. | |
| 6,428,487 B1 | 8/2002 | Burdorff et al. | |
| 6,432,065 B1 * | 8/2002 | Burdorff et al. | 600/566 |
| 6,458,121 B1 | 10/2002 | Rosenstock et al. | |
| 6,500,119 B1 | 12/2002 | West et al. | |
| 6,524,247 B2 | 2/2003 | Zhao et al. | |
| 6,558,326 B2 | 5/2003 | Pelissier | |
| 6,620,157 B1 | 9/2003 | Dabney et al. | |
| 6,632,183 B2 | 10/2003 | Bowman et al. | |
| 6,712,775 B2 | 3/2004 | Burbank et al. | |
| 6,733,458 B1 * | 5/2004 | Steins et al. | 600/461 |
| 6,752,768 B2 | 6/2004 | Burdorff et al. | |
| 6,813,512 B2 | 11/2004 | Aldefeld et al. | |
| 6,824,516 B2 * | 11/2004 | Batten et al. | 600/439 |
| 6,860,855 B2 | 3/2005 | Shelby et al. | |
| 6,911,008 B2 | 6/2005 | Pelissier et al. | |
| 6,981,941 B2 | 1/2006 | Whitman et al. | |
| 6,993,375 B2 | 1/2006 | Burbank et al. | |
| 6,996,433 B2 | 2/2006 | Burbank et al. | |
| 7,047,063 B2 | 5/2006 | Burbank et al. | |
| 7,274,325 B2 | 9/2007 | Fattah et al. | |
| 8,622,907 B2 * | 1/2014 | Malchow et al. | 600/437 |
| 2002/0151822 A1 | 10/2002 | Burdorff et al. | |
| 2002/0173719 A1 * | 11/2002 | Zhao et al. | 600/437 |
| 2002/0193705 A1 | 12/2002 | Burbank et al. | |
| 2002/0198519 A1 | 12/2002 | Qin et al. | |
| 2003/0073895 A1 * | 4/2003 | Nields et al. | 600/407 |
| 2003/0097066 A1 | 5/2003 | Shelby et al. | |
| 2003/0130711 A1 | 7/2003 | Pearson et al. | |
| 2003/0144605 A1 | 7/2003 | Burbank et al. | |
| 2003/0171678 A1 | 9/2003 | Batten et al. | |
| 2003/0181898 A1 | 9/2003 | Bowers | |
| 2003/0192557 A1 | 10/2003 | Krag et al. | |
| 2004/0030334 A1 | 2/2004 | Quick et al. | |
| 2004/0082945 A1 | 4/2004 | Clague et al. | |
| 2004/0097805 A1 | 5/2004 | Verard et al. | |
| 2004/0172017 A1 | 9/2004 | Marion et al. | |
| 2004/0181219 A1 | 9/2004 | Goble et al. | |
| 2004/0210161 A1 * | 10/2004 | Burdorff et al. | 600/566 |
| 2005/0004559 A1 | 1/2005 | Quick et al. | |
| 2005/0054900 A1 | 3/2005 | Mawn et al. | |
| 2005/0119646 A1 | 6/2005 | Scholl et al. | |
| 2005/0159677 A1 | 7/2005 | Shabaz et al. | |
| 2005/0187491 A1 | 8/2005 | Burbank et al. | |
| 2005/0197593 A1 | 9/2005 | Burbank et al. | |
| 2005/0203415 A1 | 9/2005 | Garlick et al. | |
| 2005/0261591 A1 | 11/2005 | Boctor et al. | |
| 2006/0036165 A1 | 2/2006 | Burbank et al. | |
| 2006/0084865 A1 | 4/2006 | Burbank et al. | |
| 2006/0106281 A1 | 5/2006 | Boulais et al. | |
| 2006/0149162 A1 | 7/2006 | Daw et al. | |
| 2007/0282221 A1 * | 12/2007 | Wang et al. | 600/564 |
| 2008/0004526 A1 * | 1/2008 | Gross | 600/437 |
| 2008/0132789 A1 | 6/2008 | Malchow et al. | |

FOREIGN PATENT DOCUMENTS

| | | |
|---|---|---|
| EP | 0654244 A1 | 5/1995 |
| EP | 1051948 A2 | 11/2000 |
| EP | 1053720 A1 | 11/2000 |
| EP | 1082945 A1 | 3/2001 |
| EP | 1157667 A2 | 11/2001 |
| EP | 1519472 A1 | 3/2005 |
| EP | 1527743 A2 | 5/2005 |
| GB | 2146534 A | 4/1985 |
| JP | 2002320325 A | 10/2002 |
| WO | 9315655 A1 | 8/1993 |
| WO | 9639088 A1 | 12/1996 |
| WO | 9807378 A1 | 2/1998 |
| WO | 9814129 A1 | 4/1998 |
| WO | 0224082 A2 | 3/2002 |
| WO | 0230348 A2 | 4/2002 |
| WO | 03034921 A1 | 5/2003 |
| WO | 2004110294 A1 | 12/2004 |
| WO | 2005060849 A1 | 7/2005 |

OTHER PUBLICATIONS

Force FX™ Electrosurgical Generator Instant Response to Tissue Density, Instant Response Technology, http://www.valleylab.com/PRODUCTS/fx.html, electrosurgical Generators pp. 1-4, Jun. 21, 2000.

New! Force EZ™ Electrosurgical Generator Instant Response to Tissue Density, Instant Response Technology, http://www.valleylab.com/PRODUCTS/fx.html, Electrosurgical Generators pp. 1-4, Jun. 21, 2000.

Written Opinion of the International Searching Authority for PCT/US2007/013208 mailed Feb. 25, 2008.

International Search Report for PCT/US2007/013208 mailed Feb. 25, 2008.

* cited by examiner

BIOPSY SYSTEM WITH INTEGRATED IMAGING

RELATED APPLICATIONS

This application is a continuation of U.S. patent application Ser. No. 11/810,425, filed Jun. 5, 2007, now U.S. Pat. No. 8,622,907, which is related to provisional application Ser. No. 60/810,906, filed on Jun. 5, 2006, each of which is incorporated herein in its entirety and which is relied upon for priority.

FIELD OF THE INVENTION

This invention is directed to systems and methods for imaging and removing tissue from a location within a patient and particularly to a biopsy system which has an integrated imaging system.

BACKGROUND OF THE INVENTION

Currently, to find suspicious areas or lesions, one or more imaging systems are used to locate the area or lesion of interest and may be used to guide the biopsy probe of a biopsy systems to and/or near the area or lesion of interest. Subsequently, tissue samples are removed and often, particularly in the case of breast biopsy, markers are placed at the site of the lesion removal.

Existing biopsy systems such as the EnCor® biopsy system manufactured by SenoRx, Inc. (the present assignee) and other commercially available systems are "stand alone" biopsy systems. Diagnostic imaging systems such as an ultrasound, x-ray, MRI, PET, CT, Thermal, etc. are separate devices frequently requiring substantial "floor space" in patient treatment and/or diagnosis rooms in clinical settings such as clinician offices, breast centers, hospitals, etc. Portable imaging systems are available but they can require additional operators other than the physician or other medical practitioner who is performing the biopsy.

SUMMARY OF THE INVENTION

A biopsy system embodying features of the invention includes a tissue removal system, an imaging system, an image display system and a common input console for the tissue removal system, the imaging system and the image display system.

The tissue removal system is suitable for use with one or more tissue removal probes. The imaging system is preferably an ultrasonic imaging system. The imaging system is configured to display images taken by the imaging system. The common input console is configured for imputing control or operational data to the tissue removal system, the imaging system and the image display system.

The tissue removal system has a programmable control module (microprocessor), at least one peripheral module for providing a vacuum to the tissue removal system and a plurality of connecting modules configured to receive one or more tissue removing probes. The individual probes preferably have software scripts stored in a memory device within the probe for operating the probe, controlling the functionalities of the probe and to provide pertinent information to the control module when connected thereto.

The imaging system has a programmable control module (microprocessor) for controlling the imaging system providing imaging data to a main computer module for the image display system. Preferably the imaging system has a plurality of connecting modules which allow for use of a plurality of different imaging probes (e.g ultrasound probes). For example, the ultrasound probes may have different sized or different shaped, e.g. flat or curved, ultrasonic transducer surfaces.

The biopsy system preferably has a main computer module which has communication links with the tissue removal system and the imaging system.

The common input console typically includes a key board and/or a touch screen display which allows a single operator to handle the tissue removal system the imaging system and the image display system. Moreover, the tissue removal system and the imaging system may be used alone.

The biopsy system preferably has the tissue removal system, the imaging system and the image display system mounted on a movable base such as a wheeled cart, so as to be easily transported to different locations. The biopsy system is small enough to provide a small foot-print in treatment rooms.

A number of potential diagnostic ultrasound systems are available commercially that can be used in a biopsy system embodying features of the invention, including: Sonosite, Alora, Toshiba, Siemens, GE, Philips, Acuson, ATL, HP, Medison, Shimadzu, HDAC and Hitachi. One particularly suitable ultrasound imaging system which can be packaged in a much smaller housing yet provides a high resolution, high image quality capability that may be readily adaptable to a combined biopsy system is available from the ULTRASONIX MEDICAL CORPORATION OF BRITISH COLUMBIA (Burnaby) Canada. Details of the ULTRASONIX imaging system can be found in the following patents and published applications which are incorporated herein in their entirety:

> U.S. Pat. No. 6,558,326
> U.S. Pat. No. 6,911,008
> U.S. Pat. No. 6,325,759
> U.S. Pat. Pub. No. 2002/000719 A1
> U.S. Pat. Pub. No. 2004/0193047 A1
> U.S. Pat. Pub. No. 2004/0122314 A1

A particularly suitable tissue removal system is the EnCor® and SenoCor 360® biopsy systems available from SenoRx, Inc. (the present assignee) of Aliso Viejo, Calif. Details of the EnCor® and SenoCor® biopsy systems can be found in the following U.S. Patent and published applications:

> U.S. Pat. No. 6,620,157
> U.S. Pat. Pub. No. 2004/0138653
> U.S. Pat. Pub. No. 2005/0004559
> U.S. Pat. Pub. No. 2005/0159677
> U.S. Pat. Pub. No. 2006/0149162

With the present biopsy system the clinician can identify the outline of the ultrasound image and then determine the path of tissue removal probe, e.g. an RF cutter or mechanical cutter (see listed publications and patents) on the image display. Additionally, the common input console allows the clinician to input information to the tissue control system, the imaging system and the image display system. These and other advantages will become more apparent from the following detailed description of embodiments.

DETAILED DESCRIPTION OF EMBODIMENTS

FIGS. 1-5 illustrate a biopsy system 10 that embodies features of the invention. The system 10 has a tissue removal system 11, an imaging system 12, display screen 13 and a common input console 14 with a keyboard 15 and a touch-screen display 16. The biopsy system 10 is mounted on a cart 17 which has wheels 18 at each corner for portability. The input console 14 has probe holders 20 for holding ultrasonic probes and tissue removal probes (not shown).

The tissue removal system 11 has connecting modules 21 and 22 that are configured to receive tissue removal probes (not shown) such as the probes for EnCor® and SenoCor 360® probes which are available from SenoRx, Inc., the present assignee. The imaging system 12 has connecting modules 23, 24 and 25 for connecting with different suitable ultrasonic probes, such as broadband transducers L 14-5/38, L 14-5W/60 and C 5-2/60 available from Ultrasonix Medical Corporation. The first two are linear array type transducers and the latter is a curved array type transducer.

Figure 1:
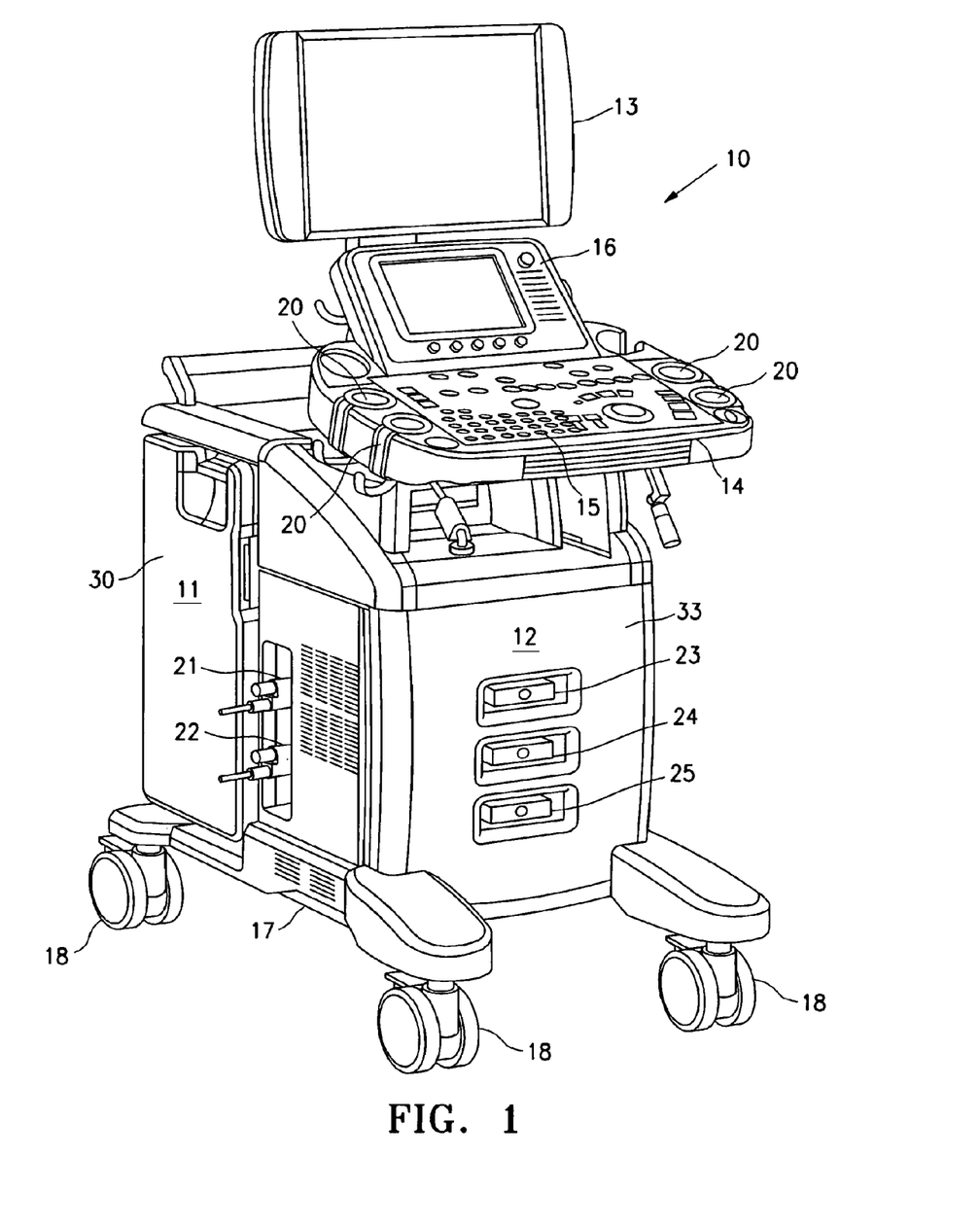
FIG. 1 is a front perspective view of a biopsy system which has a tissue removal system and an ultrasonic imaging system embodying features of the invention.
Figure 2:
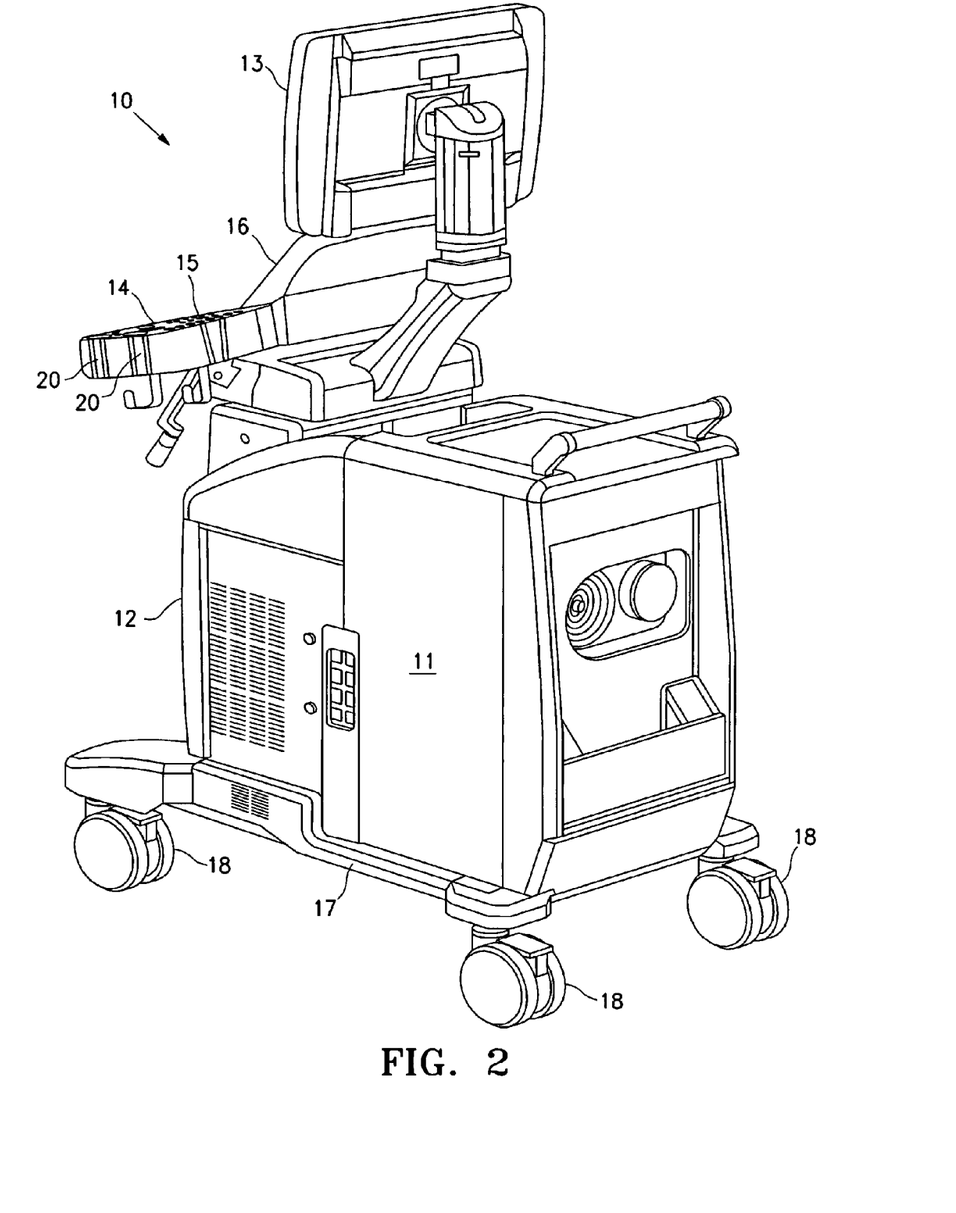
FIG. 2 is a rear perspective view of the biopsy system shown in FIG. 1 showing one side of the system.
Figure 3:
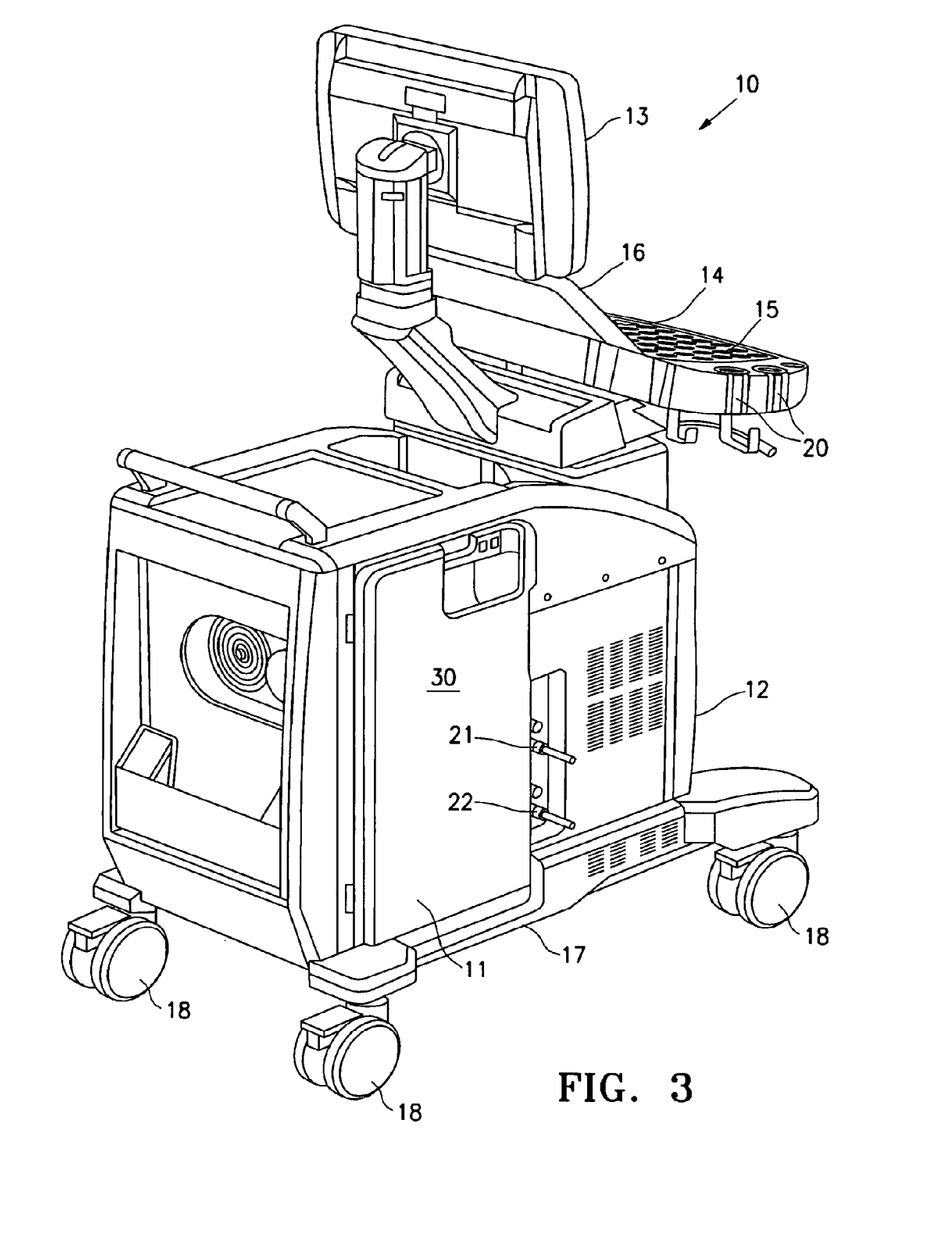
FIG. 3 is a rear perspective view of the biopsy system shown in FIG. 1 showing the side opposite to that shown in FIG. 2.
Figure 4:
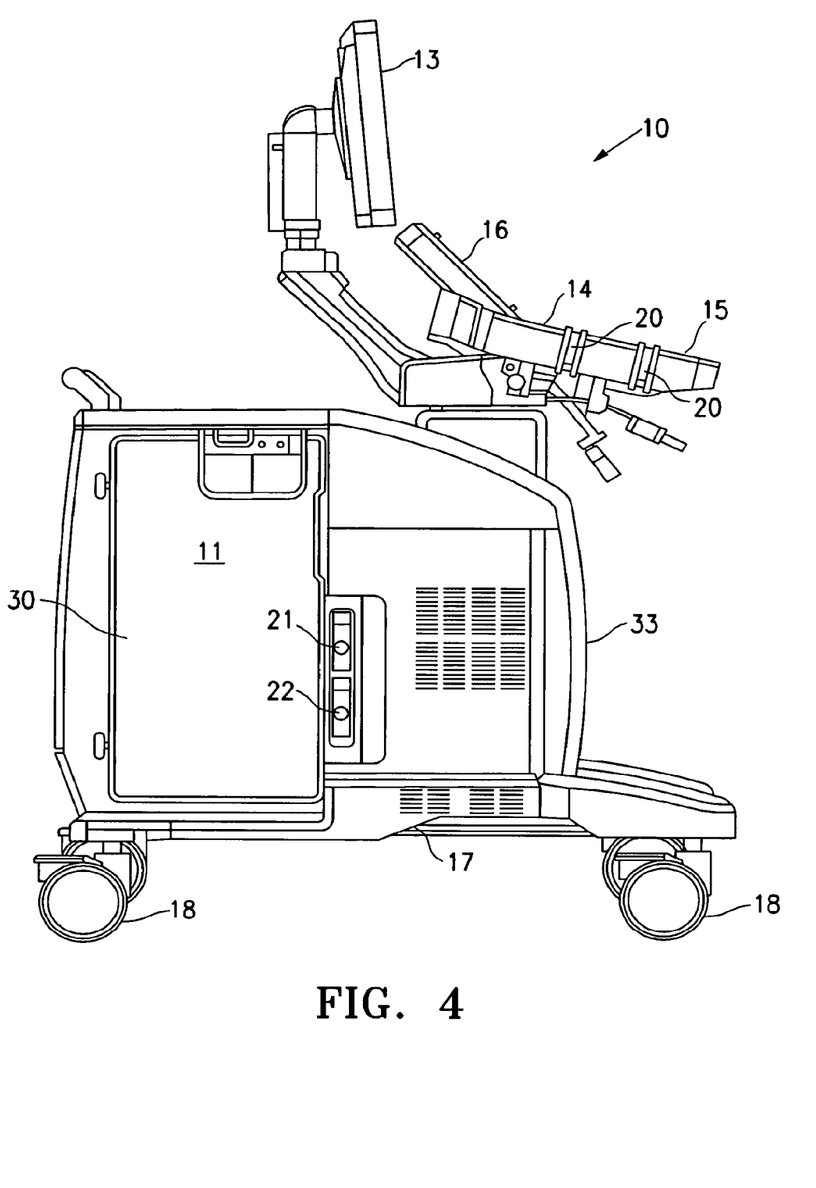
FIG. 4 is a side view of the biopsy system shown in FIG. 1.
Figure 5:
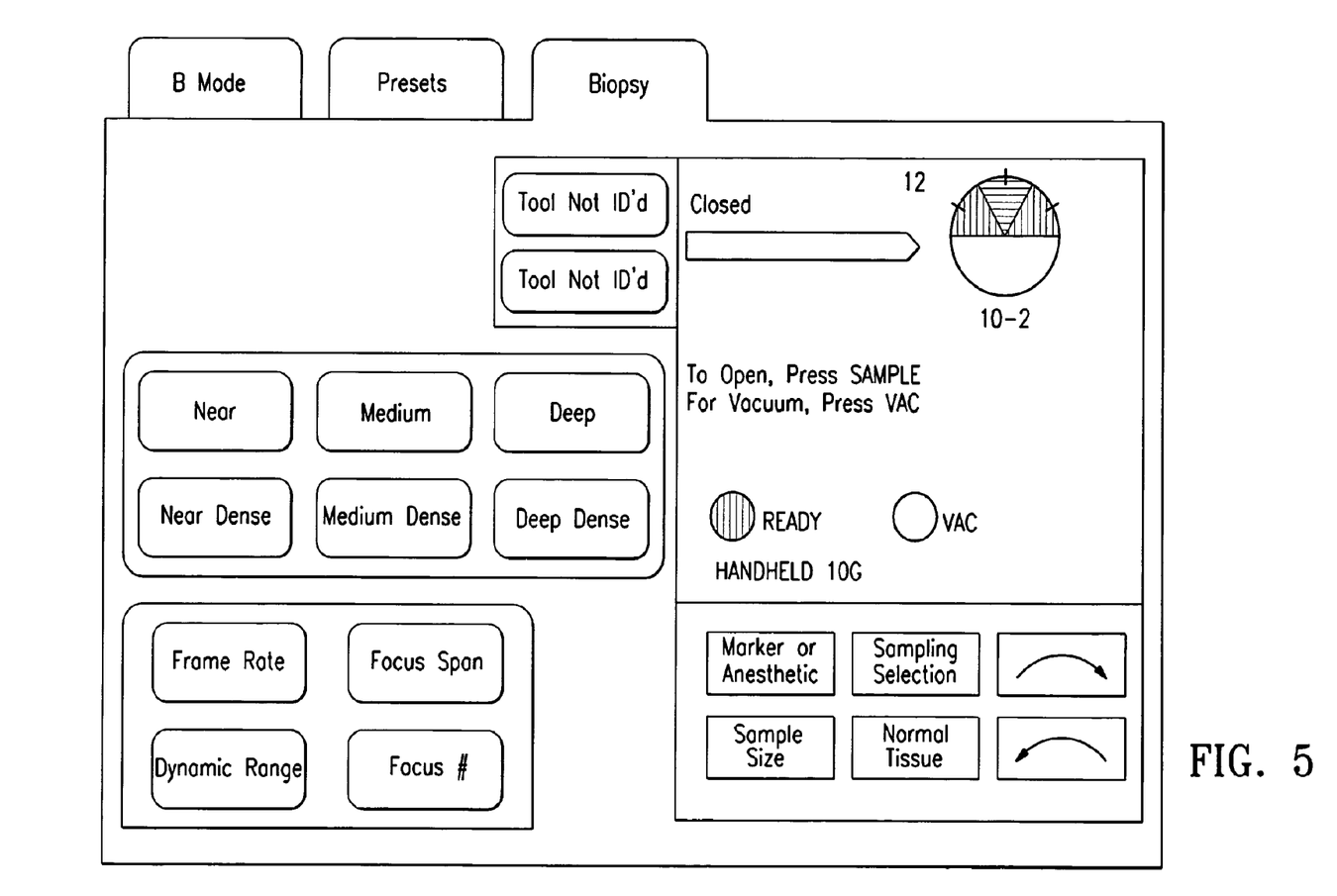
FIG. 5 depicts a touch-display screen which allows operation of both the tissue removal system and the imaging system of the biopsy system shown in FIG. 1.
Figure 6:
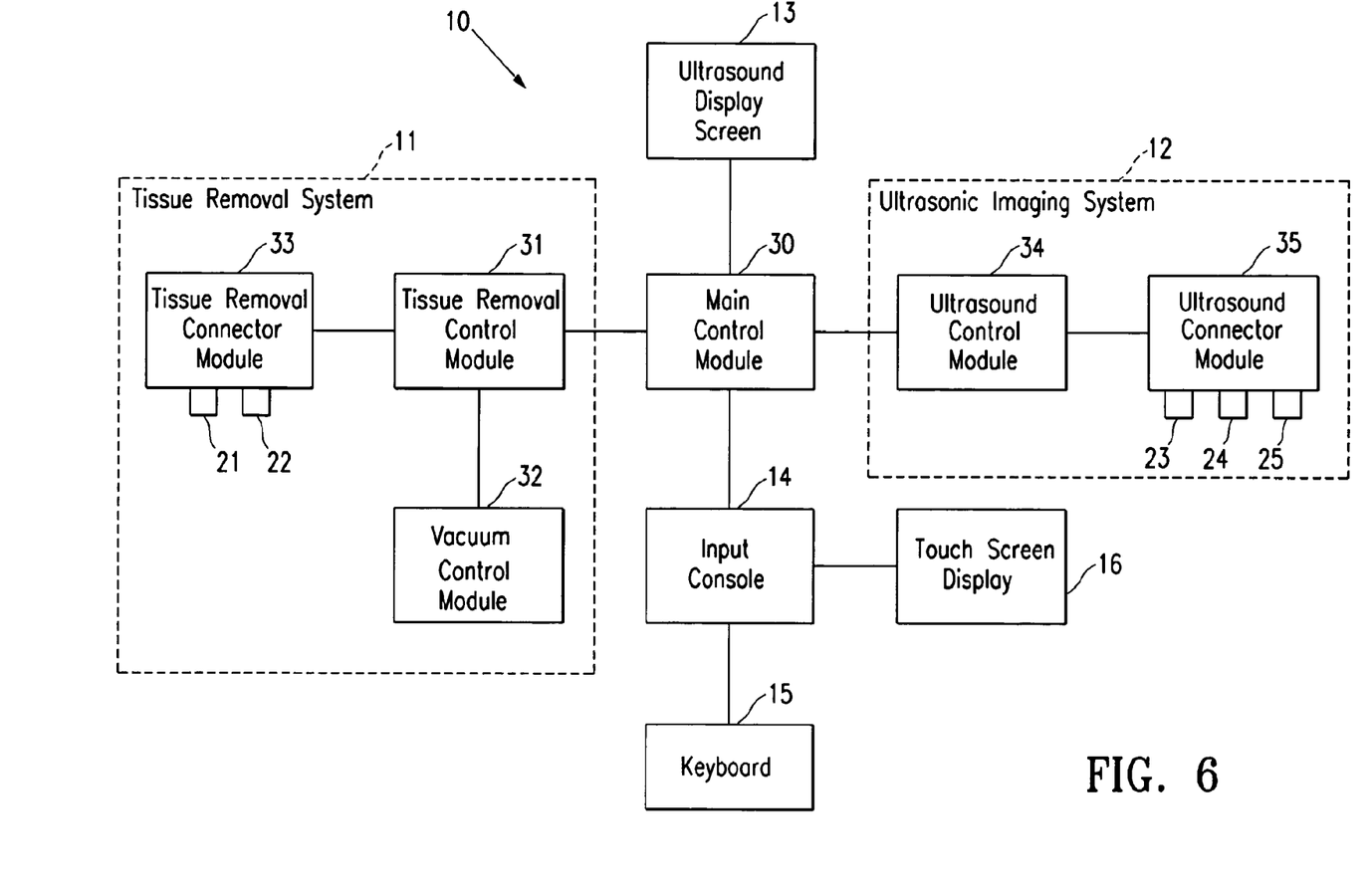
FIG. 6 is a general block diagram of a biopsy system embodying features of the invention.

FIG. 6 is a general block diagram of the biopsy system 10 shown in FIG. 1 which has a tissue removal system 11, an ultrasonic imaging system 12 and a main computer module 30 and an image display screen. The tissue removal system 11 of system 10 has a tissue removal control module 31, a vacuum module 32 for vacuum operations and tissue removal connector module 33 probe connectors 21 and 22. The vacuum module 32 has a vacuum line, a valve operated by the tissue removal control module 31 and a vacuum source (e.g. a connection to a vacuum line or a vacuum pump) which are not shown. The imaging system 12 has an ultrasound control module 34 for ultrasonic emission and reception and an interface with the main computer module 30. An ultrasound connector module 35 is in communication with the ultrasound control module and has ultrasound probe connectors 23, 24 and 25. Output from the main computer module 30 related to the imaging input data thereto from the ultrasound control module is directed through a communication link to the image display screen 13 to display ultrasonic diagnostic images from an ultrasonic probe (not shown) connected to one of the ultrasound probe connectors 23, 24 or 25.

The input console 14 is connected via a communication link to the main computer module 30 which in turn has communication links to the tissue removal control module 31 and the ultrasound control module 34. This allows the single input console 14 to be employed to control both the tissue removal system 11 and the imaging system 12. The main display screen 13 is positioned right above the input console 14 so that a single operator may easily operate both the tissue removal system 11 and the ultrasound imaging system 12 from a single console. Further details of the tissue removal system can be found in patents and published applications of SenoRx, Inc. previously referred to and incorporated herein.

The ultrasound imaging system 12 for producing ultrasound images has ultrasound control module 34 is coupled to a ultrasound connector module 35 has probe connectors 23, 24 and 24 to which may be connected an ultrasound probe (not shown) The probe generates and receives acoustic signals. The acoustic signals that are generated by the probe are directed towards a body region of a patient, e.g. breast, and some of the acoustic signals are reflected back to the probe as echo signals. The echo signals obtained by the probe are sent back to the ultrasound control module 34 which processes the echo signals to extract data that is sent to the main computer module 30. The main computer module 30 performs a display data processing in real-time which is sent to the ultrasound display screen 13 where an ultrasound diagnostic image is displayed. See U.S. Pat. No. 6,325,759, for example, which is incorporated herein by reference. Input console 14 allows the user to interact with the main computer module and modify the ultrasound configuration. Further details of the ultrasound imaging system can be found in the patents and published applications of Ultrasonix previously referred to and incorporated herein.

In the embodiment shown in FIG. 6, only the vacuum control module 32 and the tissue removal control modules 32 are shown. However, additional modules may be provided, for example modules for a temperature probe, a heart rate monitor device, a drug infusion tools, anesthesia tools, or other surgical or medical devices that may operate with the biopsy system 10. They may be connected to the tissue removal control module 31 or directly to the main computer module 30. The tissue removal devices connected to the tissue removal connector module 33 may have mechanical tissue cutting members or radio frequency (RF) powered electro-surgical cutting members for performing the surgery. It is to be understood that other peripheral modules can be of different forms and functions, and they may not be required to be physically connected to the tissue removal control module 31 or the ultrasound control module 34 or directly to the main computer module 30 so as to communicate therewith.

The tissue removal control module 31 is a microprocessor-based electrical device with built-in software functions necessary to operate various handheld devices for both tissue removal. Each handheld device preferably contains a software script, stored in a memory device within the handheld device, for operating that particular device when connected to the tissue removal control module. For example, the said software script may be stored in non-volatile memories such as erasable programmable read only memories (EPROMs), electrically erasable programmable read only memories (EEPROMs) or flash memories. When a handheld device is indirectly connected to the tissue removal control module 31, the software script within the handheld device will be downloaded into the tissue removal control module. This software script will enable the tissue removal control module 31 to control the functionalities of a particular handheld device. Connection to the main computer module 30 allows the touch screen 14 to display its pertinent information and allow control input through either the touch screen or the keyboard 15. During the operation of a handheld device, a graphical user interface (GUI) software will display information on the touch screen 14 relevant to the operation of the tissue removal control module 31 and the handheld device to the operator. It is understood by those skilled in the art that the information displayed may vary depending upon the type of handheld device connected, the operational state of the handheld device as well as other environmental factors affecting the operation of both the handheld device and the main computer module 30.

It is understood that although the various modules and the handheld devices for either the tissue removal system 11 or the ultrasound image system 12 may be interconnected through wired connections (including connector modules and wires) for their operations, the communication links can be easily implemented through wireless communications. However, the conventional wired connections have certain advantages such as low signal interferences, but the wireless technology can turn the operation of the handheld device to a more mobile operation, which benefits the operator as well. For example, almost all the control signals can be sent through a predetermined wireless communication channel using technologies such as Bluetooth or 802.11 compliant wireless technologies. When the handheld device is battery powered, then the operation may be completely mobile. It is also practical that the wired communication channels may be used together with the wireless communication channels so that the tissue removal control module can take advantage of the available wireless technologies for providing convenience to the operator, while still benefiting from using some conventional wired technologies. In short, while the examples provided herein illustrate embodiments having features of the invention, it should be understood that communications between devices can take various forms and the main computer module 30, the tissue removal control module 31 and the ultrasound control module 33 are designed to use the most practical technologies for fulfilling the need of the operators.

The biopsy system may be powered by a single power source (not shown) or can have multiple power sources for various functions. For example, the tissue removal system 11 and the ultrasound imaging system 12 may have separate power sources.

While particular forms of the invention have been illustrated and described herein, it will be apparent that various modifications and improvements can be made to the invention. For example, the discussion herein has focused on ultrasound imaging. Those having ordinary skill in the art will recognize that other imaging systems may be employed, for example x-ray or mammographic imaging. To the extent not previously described, the various elements of the biopsy system may be made from conventional materials used in similar devices. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "manufacture", "portion", "section", "steps" and words of similar import when used herein shall not be construed as invoking the provisions of 35 U.S.C. §112(6) unless the following claims expressly use the terms "means for" or "step for" followed by a particular function without reference to a specific structure or action. All patents and all patent applications referred to above are hereby incorporated by reference in their entirety.

What is claimed is:

1. A structurally integrated biopsy system, comprising:
   a movable base having wheels to facilitate movement of the structurally integrated biopsy system;
   a tissue removal system mounted to the movable base, the tissue removal system including a probe connector configured to connect to a tissue removal probe;
   an ultrasound imaging system directly connected to the tissue removal system, the ultrasound imaging system mounted to the movable base, the ultrasound imaging system being configured to generate an ultrasound image of a body region of a patient, and having an image display system having an image display screen to display ultrasound images taken by the ultrasound imaging system; and
   a controller mounted to the movable base, the controller configured to be in communication with each of the tissue removal system and the ultrasound imaging system to both provide control information for the ultrasound imaging system and provide control information for the tissue removal system in the structurally integrated biopsy system.

2. The structurally integrated biopsy system of claim 1, wherein the controller includes a main computer module and an input console, the input console being communicatively coupled to each of the tissue removal system and the ultrasound imaging system.

3. The structurally integrated biopsy system of claim 1, wherein the ultrasound imaging system and the tissue removal system are configured to be operational simultaneously.

4. The structurally integrated biopsy system of claim 1, wherein the tissue removal system includes a tissue removal control module communicatively coupled to the controller, and a tissue removal connector module configured to form a first communication link between the tissue removal probe and the tissue removal control module.

5. The structurally integrated biopsy system of claim 4, wherein the tissue removal system includes a vacuum control module communicatively coupled to the controller.

6. The structurally integrated biopsy system of claim 5, comprising a second communication link communicatively coupled between the vacuum control module and the tissue removal control module.

7. The structurally integrated biopsy system of claim 1, wherein the ultrasound imaging system includes an ultrasound control module and an ultrasound imaging probe, and a connector module configured to form a communication link between the ultrasound imaging probe and the ultrasound control module.

8. The biopsy structurally integrated system of claim 7, wherein an ultrasound image is displayed on the image display screen based upon data received from the ultrasound imaging probe.

9. The structurally integrated biopsy system of claim 1, wherein the controller includes an input console configured to provide control information to an ultrasound control module of the ultrasound imaging system and is configured to provide control information to a tissue removal control module of the tissue removal system.

10. The structurally integrated biopsy system of claim 1, wherein the controller includes a main computer module communicatively coupled by a respective communication link to each of the tissue removal system and the ultrasound imaging system.

11. The structurally integrated biopsy system of claim 10, wherein the ultrasound imaging system includes an interface module configured to facilitate communication between an ultrasound control module of the ultrasound imaging system and the main computer module.

12. The structurally integrated biopsy system of claim 1, wherein the tissue removal system has a plurality of connector modules configured to facilitate connecting different tissue removal probes to the tissue removal system.

13. The structurally integrated biopsy system of claim 1, wherein the ultrasound imaging system has a plurality of connector modules configured to facilitate connecting different imaging probes to the ultrasound imaging system.

14. The structurally integrated biopsy system of claim 1, wherein the movable base is a wheeled cart.

15. The structurally integrated biopsy system of claim 1, wherein the tissue removal system is contained within a first housing on the movable base.

16. The structurally integrated biopsy system of claim 15, wherein the ultrasound imaging system is contained within a second housing on the movable base.

17. The structurally integrated biopsy system of claim 16, wherein the controller includes a main computer module that is contained within the second housing.

18. The structurally integrated biopsy system of claim 15, wherein a vacuum control module is contained within the first housing for the tissue removal system.

19. A structurally integrated biopsy system, comprising:
- a wheeled cart configured to facilitate movement of the structurally integrated biopsy system;
- a tissue removal system mounted to the wheeled cart, the tissue removal system having a plurality of connector modules configured to facilitate connecting different tissue removal probes to the tissue removal system;
- an ultrasound imaging system mounted to the wheeled cart, the ultrasound imaging system mounted to the movable base, the ultrasound imaging system having a plurality of connector modules configured to facilitate connecting different imaging probes to the ultrasound imaging system, the ultrasound imaging system being configured to generate an ultrasound image of a body region of a patient based upon data received from a connected ultrasound imaging probe, and having an image display screen to display ultrasound images taken by the ultrasound imaging system; and
- a controller mounted to the wheeled cart, the controller configured to be in communication with each of the tissue removal system and the ultrasound imaging system to both provide control information for the ultrasound imaging system and provide control information for the tissue removal system in the structurally integrated biopsy system.

20. The structurally integrated biopsy system of claim 19, wherein the controller includes a main computer module and an input console, the input console being communicatively coupled to each of the tissue removal system and the ultrasound imaging system, and wherein the tissue removal system and the ultrasound imaging system are configured to be operational simultaneously.

* * * * *